(12) United States Patent
Klein et al.

US006180398B1

(10) Patent No.: US 6,180,398 B1
(45) Date of Patent: Jan. 30, 2001

(54) **TWO-STEP IMMUNIZATION PROCEDURE AGAINST THE PYRAMYXOVIRIDAE FAMILY OF V

OTHER PUBLICATIONS

Taylor, J., Trimarchi, C., Weinberg, R., Languet, B., Guillemin, F., Desmettre, Ph., Paoletti, E. (1991) Efficacy studies on a canarypox–rabies recombinant. Vaccine 9, 190–193.

Taylor, J., Weinberg, R., Tartaglia, J., Richardson. C., Alkatib, G., Briedis, D., Appel, M., Norton, E., Paoletti, E. (1992) Nonreplicating viral vectors as potential vaccines: recombinant canarypox virus expressing measles virus fusion (F) and hemagglutinin (HA) glycoproteins. Virology 187, 321–328.

Tartaglia, J., Taylor, J., Cox, W.I., Audonnet, J.–C., Perkus, M.E., Raedelli, A., de Guili Morghen, C., Meignier, B., Riviere, M., Weinhold, K,, Paoletti, E. (1993) Novel poxvirus strains as research tools and vaccine vectors. In AIDS Research Reviews (W.C. Koff, F. Wong–Staal, and R.C. kennedy, eds.), vol. 3, Marcel Dekker, New York, 361–378.

Cadoz, M., Strady, A. Meignier, B., Taylor,J., Taryaglia, J., Paoletti, E., Plotkin, S. (1992) Immunization with canarypox virusexpressing rabies glycoproteins. Lancet 339, 1429–1432.

Pialoux, G., Excler, J.–L., Riviere, Y., Gonzalez–Canali, G., Feuillie, V., Coulaud, P., Gluckman, J.–C., Matthews, T.J., Meignier, B., Kieny, M.–P., Gonnet, P., Diaz, I., Meric, C., Paoletti, E., Tartaglia, J., Salomon, H., Plotkin, S. (1995) A primeboost approach to HIV preventive vaccine using a recombinant canarypox virus expressing glycoprotein gp160 (MN) followed by a recombinant glycoprotein 160 (MN/Lai). AIDS Res. Hum. Retrovir. 11, 373–381.

Mullis, K., Ferre, F., and Gibbs, R. (1994) The Polymerase Chain Reaction. Boston: Birkhauser press.

Perkus, M., Limbach, K. and Paoletti, E. (1989) Cloning and expression of foreign genes in vaccinia virus, using a host range selection system. J. Virol. 63: 3829–3836.

Yuen, L. and Moss, B. (1987) PNAS 84: 6417–6421.

Goebel, S., Johnson, G., Perkus, M., Davis, S., Winslow, J., and Paoletti, E. (1990), The complete DNA sequence of vaccinia virus, Virology 179: 247–266.

Prince, G.A. et al. 1978, Am J. Pathol. 93: 771–790.

Fulginiti, V.A., Eller, J.J., Sieber, O.F., Joyner, J.W., Minamitani, M. and Meiklejohn, G. (1969) Am. J. Epidemiol. 89 (4), 435–448.

Chin, J., Magoffin, R.L., Shearer, L.A., Schieble, J.H. and Lennette, E.H. (1969) Am. J. Epidemiol. 89 (4), 449–463.

Jensen, K.E., Peeler, B.E. and Dulworth, W.G. (1962) J. Immunol. 89, 216–226.

Murphy, B.R., Prince, G.A., Collins, P.L., Van Wyke Coelingh, K., Olmsted, R.A., Spriggs, M.K., Parrott, R.H., Kim, H.–Y., Brandt, C.D. and Chanock, R.M. (1988) Vir. Res. 11, 1–15.

Hall, S.L., Sarris, C.M., Tierney, E.L., London, W.T., and Murphy, B.R. (1993) J. Infect. Dis. 167, 958–962.

Belshe, R.B., Karron, R.A., Newman, F.K., Anderson, E.L., Nugent, S.L., Steinhoff, M., Clements, M.L., Wilson, M.H., Hall, S.L., Tierney, E.L. and Murphy, B.R. (1992) J. Clin. Microbiol. 30 (8), 2064–2070.

Hall, S.L., Stokes, A., Tierney, E.L., London, W.T., Belshe, R.B., Newman, F.C. and Murphy, B.R. (1992) Vir. Res. 22, 173–184.

Van Wyke Coelingh, K.L., Winter, C.C., Tierney, E.L., London, W.T. and Murphy, B.R. (1988) J. Infect. Dis. 157 (4), 655–662.

Ray, R., Novak, M., Duncan, J.D., Matsuoka, Y. and Compans, R.W. (1993) J. Infect. Dis. 167, 752–755.

Ray, R., Brown, V.E. and Compans, R.W. (1985) J. Infect. Dis. 152 (6), 1219–1230.

Ray, R. and Compans, R.W. (1987) J. Gen. Virol. 68, 409–418.

Ray, R., Glaze, B.J., Moldoveanu, Z. and Compans, R.W. (1988) J. Infect. Dis. 157 (4), 648–654.

Ray, R., Matsuoka, Y., Burnett, T.L., Glaze, B.J. and Compans, R.W. (1990) J. Infect. Dis. 162, 746–749.

Ray, R., Glaze, B.J. and Compans, R.W. (1988) J. Virol. 62 (3), 783–787.

Ewasyshyn, M., Caplan, B., Bonneau A.–M., Scollard, N., Graham, S., Usman, S. and Klein, M. (1992) Vaccine 10 (6), 412–420.

Ambrose, M.W., Wyde, P.R., Ewasyshyn, M., Bonneau, A.–M., Caplan, B., Meyer, H.L. and Klein, M. (1991) Vaccine 9, 505–511.

Kasel, J.A., Frank, A.L., Keitel, W.H., Taber, L.H., Glezen W.P.J. Virol. 1984; 52:828–32.

Lehman, D.J., Roof, L.L., Brideau, R.J., Aeed, P.A., Thomsen, D.R., Elhammer, A.P., Wathen, M.W. and Homa, F.L. (1993) J. Gen. Virol. 74, 459–469.

Brideau, R.J., Oien, N.L., Lehman, D.J., Homa, F.L. and Wathen, M.W. (1993) J. Gen. Virol. 74, 471–477.

Ebata, S.N., Prevec, L., Graham, F.L. and Dimock, K. (1992) Vir. Res. 24, 21–33.

Hall, S.L., Murphy, B.R. and Van Wyke Coelingh, K.L. (1991) Vaccine 9, 659–667.

Crowe et al. "A comparison in chimpanzees of the immunogenicity and efficacy of live attenuated respiratory syncitial virus (RSV) temperature–sensitive mutant vaccines and vaccinia virus recombinanyts that express the surface glycoproteins of RSV". Vaccine, 1993.*

McIntosh et al. "Respiratory Syncitial Virus". In Virology, edited by Fields et al. New York, Raven Press. pp. 1045–1072, 1990.*

Tristram et al. "Respiratory Syncitial Virus Vaccines: Can we Improve on Nature ?". Pediatric Annals. vol. 22:715–718, Dec. 12, 1993.*

Perkus et al. "Recombinant Vaccinia Virus: Immunization Against Multiple Pathogens". Science. vol. 229, pp. 981–984, Sep. 1985.*

* cited by examiner

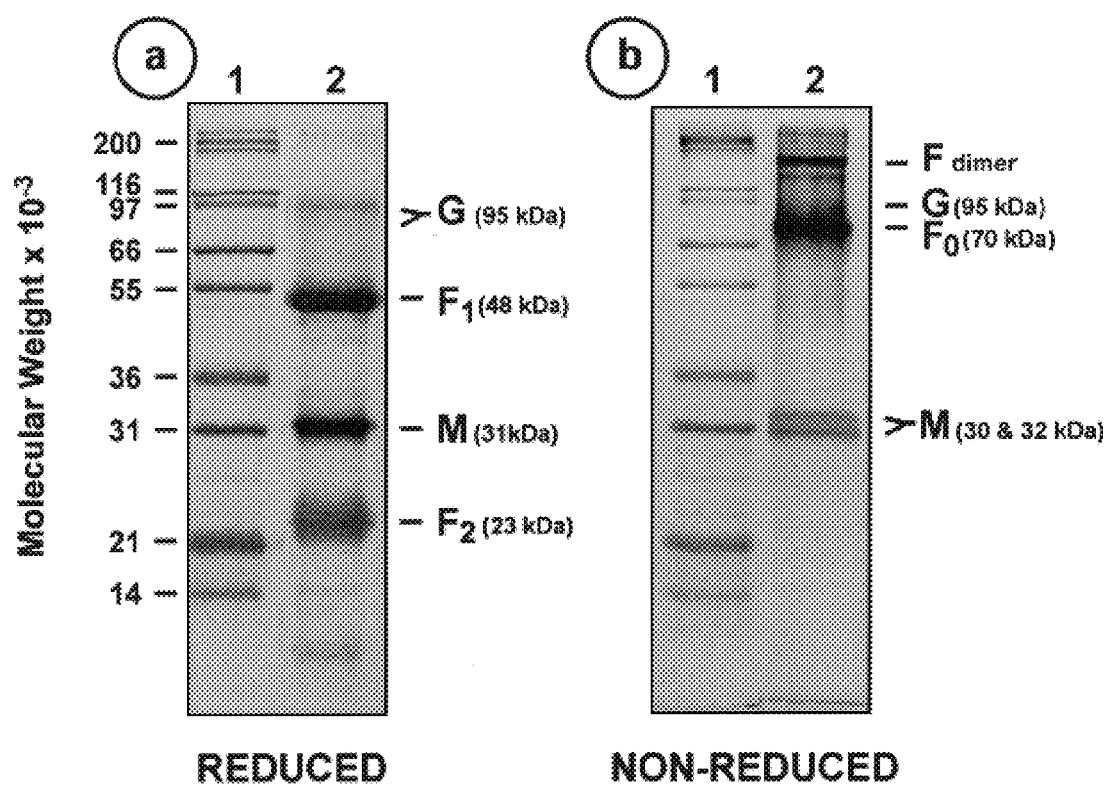
Figure 1 - SDS-PAGE Analysis of RSV Subunit (silver stain)
Lane 1 = Molecular Weight Standards
Lane 2 = RSV Subunit

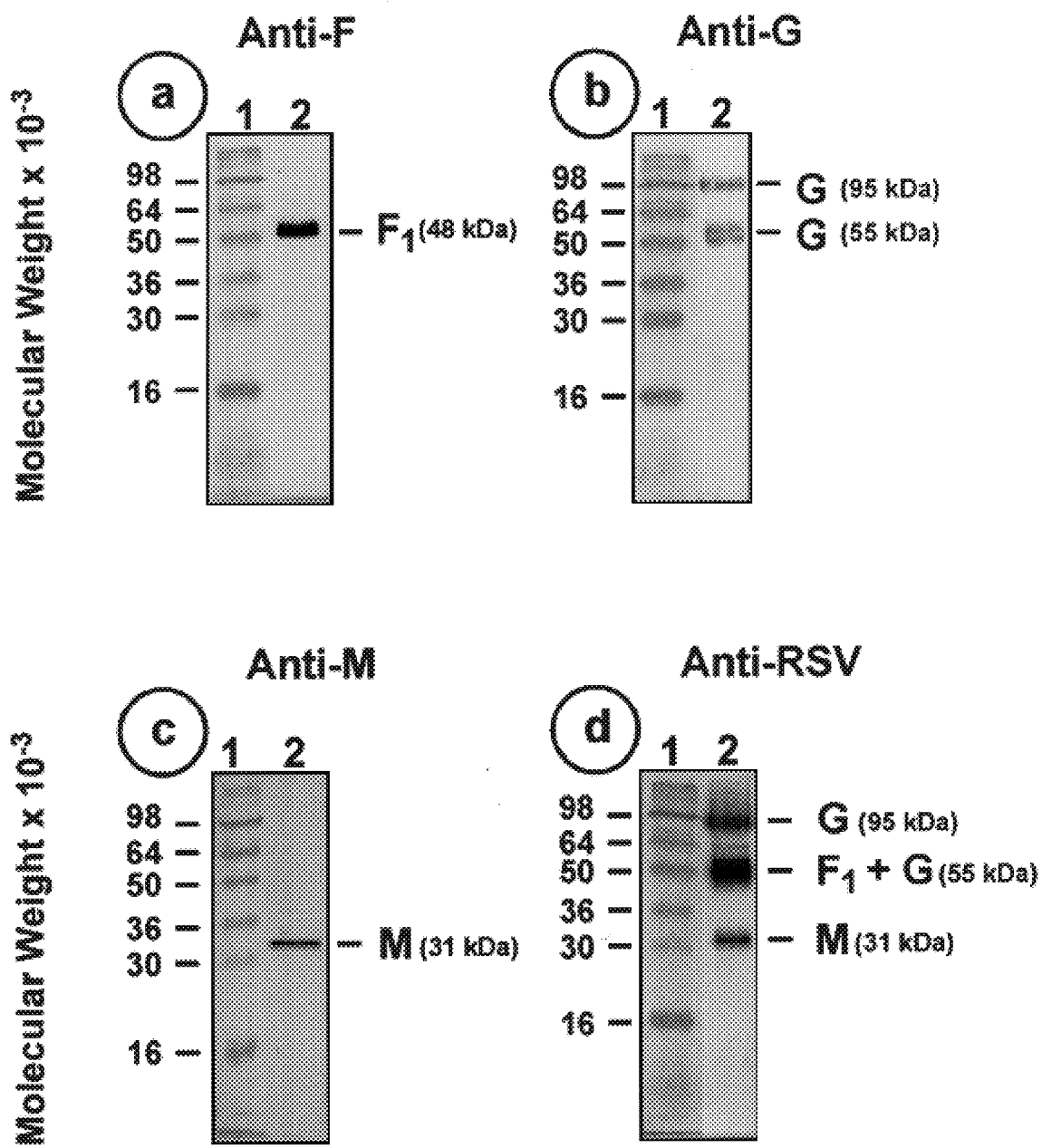

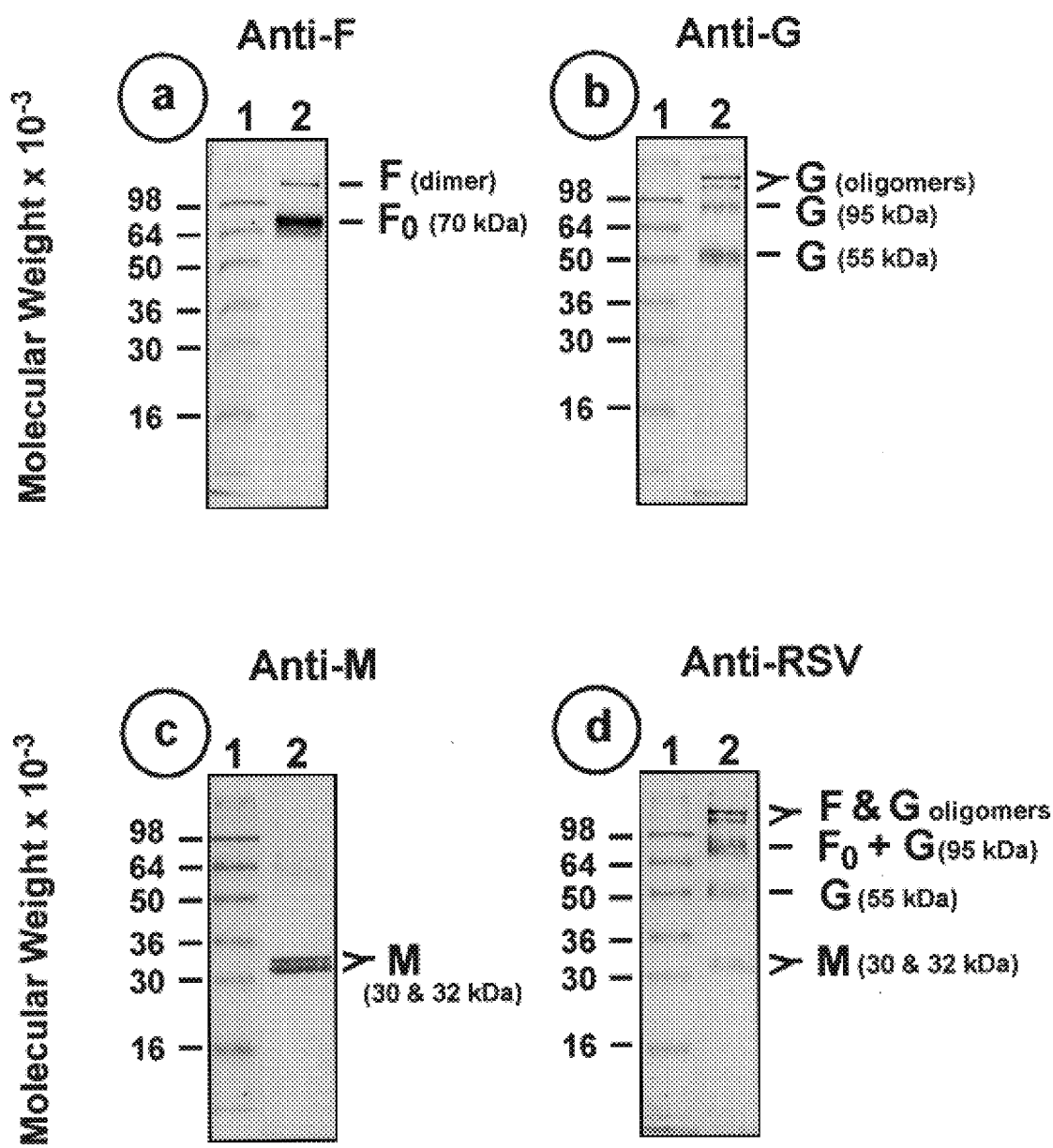

FIG.4

Nucleotide sequence of the vCP181 (ALVAC-F) H6 promoted RSV-F insertion and flanking sequences. The H6 promoter begins at position 202. RSV-F starts at position 326 and ends at position 2048.

```
1     ATACATAATGGATTTTGTTATCATCAGTTATATTAACATAAGTACAATAAAAGTATTA
61    AATAAAAATACTTACTTACGAGAAAAATGACTAATTAGCTATAAAACCCGGCCGCTTTTT
121   ATTAATTAATTAACCCGGGTTAATTAATTAGTTATTAGACAAGGTGAAACGAAACTATT
181   TGTAGCTTAATTAATTAGAGCTTCTTTATTCTATACTTAAAAGTGAAAATAACAAA
241   GGTTCTTGAGGGTGTTAAATGAAAGCGAGAAATAATCATAAATTATTTCATTATCG
301   CGATATCCGTTAAGTTTGTATCGTAATGGAGTGCTAATCCTCAAAGCAAATGCAATTAC
361   CACAATCCTGCTGCAGTCACATTTGCTTTGCTCTAGTCAAACATCACTGAAGAATT
421   TTATCAATCAGTGCAGTAGCAGTTAGCAAGGCTATCTTAGTGCTCTAAGAACTGGTTG
481   GTATACTAGTGTTATAACTATAGAATTAAGGAAAATATCAAGGAAATAAAGTGTAATGGAAC
541   AGATGCTAAGGTAAAGTAAATTGATAAACAAGAATTAGATAAAATATAAAATGTAACAGA
601   ATTGCAGTTGCTCATGCAAAGCACACTCAACAATCAGCAAACAATCGAGCCAGAAGAACTACC
661   AAGGTTTATGAATTATACACTCAACATTATACACCAATGGGATCTGCAATCGCCAGTGGCAT
721   AAGGAAAAGAAGATTCTGTTTTTGTTAGGAGAAGTGAACAAGATCAAAAGTGCTCTACT
781   TGCTGTATCTAAGGTCCTGCACTGAGAAGTAGTCAGCTTATCAATGGAGTTAGTGTCTTAACCAGCAAAGT
841   ATCCACAAACAAGGCCGTAGTCAGTTCAGCTTATCAATGGAGTTAGTGTCTTAACCAGCAAAGT
901   GTTAGACCTCAAAAACTATAGATAAACAATTGTTACCTATTGTGAATAAGCAAGCTG
961   CAGAATATCAAATATAGAAACTGTAGAGTTCCAACAAAGAACAACAGACTACTAGA
1021  GATTACCAGGAATTAGTGTTAATGCAGGTGTAACTGCACCTGTAAGCACTTACATGTT
1081  AACTAATAGTGAATTATTGTCATTAATCAATGCCTATAACAAATGATCAGAAAAA
1141  GTTAATGTCCAACAATGTTCAAATAGTTAGACAGCAAAGTTACTCTATCATGTCCATAAT
1201  AAAAGAGGAAGTCTTAGCATATGTAGTACAATTACCACTATATGGTGTGATAGATACACC
```

FIG.4 con't

```
1261 TTGTTGGAAATTACACACATCCCCTCTATGTACAACAACACAAAAGAAGGGTCAAACAT
1321 CTGTTTAACAAGAACTGACAGAGGATGGTACTGTGACAATGCAGGATCAGTATCTTCTT
1381 CCCACAAGCTGAAACATGTAAAGTTCAATCGAATCGAGTATTTGTGACACAATGAACAG
1441 TTTAACATTACCAAGTGAACATGTGAAATCTCTGCAAGTAATTCAATCCAAATATGA
1501 TTGTAAAATTATGACTTCAAAAACAGATGTAAGCAGCTCCGTTATCACATCTCTAGGAGC
1561 CATTGTGTCATGCTATGGCAAAACTAAATGTACAGCATCCAATAAAAATCGTGGAATCAT
1621 AAAGACATTTCTAACGGGGTGTGATTATGTAAATAAGCAAGAGGCAAAAGTCTATGTAAAGGTGA
1681 AGGTAACACATTATATATTTCTATGACCCATTAGTAATTCCCCTCTGATGAATTGATGCATCAAT
1741 ACCAATAATAAATTTCTATGACCCATTAGTAACCAGAGTTAGCATTTATTCGTAAATCCGATGAATT
1801 ATCTCAAGTCAAGAGAAATGCTGGTAAATCAACACAAATATCATGATAACTACTATAATTAT
1861 ATTACATCATGTAAATATTGTTATCATTAATTGTGTTGGACTGCTCCTATACTGTAAGGC
1921 AGTGATTATAGTAATAATGCAGGATCAACTGAGTGGTATAAATAATATTGCATT
1981 CAGAAGCACACCAGTCACACTAAGCAAGGATCAACTGAGTCAACTGAGTGGTATAAATAATATTGCATT
2041 TAGTAACTGAAAGCTTCTAGCTAATTTTATAGCGGCCGGGCTGCAGCTCGAGGAA
2101 TTCTTTTATTGATTAACTAGTCAAATGAGTATATAATTGAAAGTAAAATATAAAT
2161 CATATATAATGAAAC
```

FIG.5

Nucleotide sequence of the vP1000 (NYVAC-F) H6 promoted RSV-F insertion and flanking sequences. The H6 promoter begins at position 575. RSV-F starts at position 699 and ends at position 2421.

1 GTCGACGATTGTTCATGATGGCAAGATTTATATATCTGGAGGTTACAACAATAGTAGTGT
61 AGTTAATGTAATATCGAATCTAGTCCTTAGCTATAATCCGATATATGATGAATGGACCAA
121 ATTATCATCATTAAACATTCCTAGAATTAATCCCGCTCTATGGTCAGCGCATAATAAATT
181 ATATGTAGGAGGAGGAATATCTGATGATGTTCGAACTAATACATCTGAAACATACGATAA
241 AGAAAAAGATTGTTGGACATTGGATAATGGTCACGTGTTACCACGCAATTATATAATGTA
301 TAAATGCGAACCGATTAAACATAAATATCCATTGGAAAAACACAGTACACGAATGATTT
361 TCTAAAGTATTTGGAAAGTTTTATAGGTAGTTGATAGAACAAAATACATAATTTTGTAAA
421 AATAAATCACTTTTTATACTAATATTTAATTAATTAAGCTTGGTACCCTCGAGGGATCCC
481 CCGGCCGCTTTTTATTAATTAATTAACCCGGGTTAATTAATTAGTTATTAGACAAGGTGA
541 AAACGAAACTATTTGTAGCTTAATTAATTAGAGCTTCTTTATTCTATACTTAAAAAGTGA
601 AAATAAATACAAAGGTTCTTGAGGGTTGTGTTAAATTGAAAGCGAGAAATAATCATAAAT
661 TATTTCATTATCGCGATATCCGTTAAGTTTGTATCGTAATGGAGTTGCTAATCCTCAAAG
721 CAAATGCAATTACCACAATCCTCGCTGCAGTCACATTTTGCTTTGCTTCTAGTCAAAACA
781 TCACTGAAGAATTTTATCAATCAACATGCAGTGCAGTTAGCAAAGGCTATCTTAGTGCTC
841 TAAGAACTGGTTGGTATACTAGTGTTATAACTATAGAATTAAGTAATATCAAGGAAAATA
901 AGTGTAATGGAACAGATGCTAAGGTAAAATTGATAAAACAAGAATTAGATAAATATAAAA
961 ATGCTGTAACAGAATTGCAGTTGCTCATGCAAAGCACATCAGCAGCAAACAATCGAGCCA
1021 GAAGAGAACTACCAAGGTTTATGAATTATACACTCAACAATACCAAAAAAACCAATGTAA
1081 CATTAAGCAAGAAAAGGAAAAGAAGATTTCTTGGTTTTTGTTAGGTGTTGGATCTGCAA

FIG.5 con't

```
1141 TCGCCAGTGGCATTGCTGTATCTAAGGTCCTGCACTTAGAAGGAGAAGTGAACAAGATCA
1201 AAAGTGCTCTACTATCCACAAACAAGGCCGTAGTCAGCTTATCAAATGGAGTTAGTGTCT
1261 TAACCAGCAAAGTGTTAGACCTCAAAACTATATAGATAAACAATTGTTACCTATTGTGA
1321 ATAAGCAAAGCTGCAGAATATCAAATATAGAAACTGTGATAGAGTTCCAACAAAGAAACA
1381 ACAGACTACTAGAGATTACCAGGGAATTTAGTGTTAAGTGCAGGTGTAACTACACCTGTAA
1441 GCACTTACATGTTAACTAATAGTGAATTGAATTGTCATTAATCAATGATATGCCTATAACAA
1501 ATGATCAGAAAAGTAATGTCCAACAATGTTCAAATAGTTAGACAGCAAAGTTACTCTA
1561 TCATGTCCATAATAAAAGAGGAAGTCTTAGCATATGTAGTACAATTACCACTATATGGTG
1621 TGATAGATACACCTTGTTGGAAATTACACACACATCCCCTCTATGTACAACAACACAAAG
1681 AAGGGTCAAACATCTGTTTAACAAGACTGAAACATGTAAGTTCAATGCAATGCAGGAT
1741 CAGTATCTTTCTTCCCACAGTTAACATTACCAAGTGAAATCGAGTATTTGTG
1801 ACACAATGAACAGTTAACATTACCAAGTGAAGTAAATCTCTGCAATGTTGACATATTCA
1861 ATCCCAAATATGATTGTAAAATTATGACTTCAAAAACAGATGTAAGCAGCTCCGTTATCA
```

FIG.5 con't

```
1921 CATCTCTAGGAGCCATTGTGTCATGCTATGGCAAAACTAAATGTACAGCATCCAATAAAA
1981 ATCGTGGAATCATAAAGACATTTCTAACGGGTGTGATTATGTATCAAATAAGGGGTGG
2041 ACACTGTGTCTAGGTAACACATTATATTATGTAAATAAGCAAGAAGGCAAAGTCTCT
2101 ATGTAAAAGGTGAACCAATAATAAATTTCTATGACCCATTAGTTATTCCCCTCTGATGAAT
2161 TTGATGCATCAATATCTCAAGTCAATGAGAAGATTAACCAGAGTTTAGCATTATTCGTA
2221 AATCCGATGAATTATTACATCATGTCTGGTAAATCAACACAAATATCATGATAA
2281 CTACTATAATTATATGATTATAGTAATTGTTATCATTAATTGCTGTGGACTGCTCC
2341 TATACTGTAAGGCCAGAAGCACACCAGTCACACTAAGCAAGGATCAACTGAGTGGTATAA
2401 ATAATATTGCATTAGTAACTGAAAGCTTCTAGCTAATTTTTATAGCGGGCCGGGTA
2461 GCTAGCTAATTTTCTTTTTACGTATTATATATGTAATAAACGTTCACGTAAATACAAAAC
2521 AGAGAACAAAGTCTAGATTTTTGACTTACATAAATGTCTGGGATAGTAAATCTATCATA
2581 TTGAGCGGACCATCTGGTTCAGGAAAGACAGCCATAGCCAAAAGACTATGGAATATATT
2641 TGGATTTGTGTGTCCCATACCACCTAGATTTCCTCGTCCTATGGAAACGAGAAGGTGTCGA
2701 TTACCATTACGTTAACAGAGAGGCCATCTGGAAGGGAATAGCCGCGGAAACTTTCTAGA
2761 ACATACTGAGTTTTTAGGAAATATTTACGGAACTCTAAAACTGCTGTGAATACAGCGGC
2821 TATTAATAATCGTATTTGTGTGATGGATTTAAACATCGACGGTGTTAGAAGTTTTAAAAA
2881 TACTTACCTGCAGAAGCTT
```

* Placebo control animals (groups 6,7,8,) were immunized according to the protocol outlined in Table 1.

TWO-STEP IMMUNIZATION PROCEDURE AGAINST THE PYRAMYXOVIRIDAE FAMILY OF VIRUSES USING RECOMBINANT VIRUS AND SUBUNIT PROTEIN PREPARATION

FIELD OF INVENTION

The present invention relates to the field of immunology and, in particular, to a vaccination procedure for protection of a host against disease caused by infection with a virus of the paramyxoviridae family, particularly respiratory syncytial virus (RSV).

BACKGROUND TO THE INVENTION

Human parainfluenza virus type 1, 2, 3 and human respiratory syncytial virus (RSV) have been identified as the major viral pathogens responsible for severe respiratory tract infections in infants and young children (ref. 1 to 3—Throughout this specification, various references are referred to in parenthesis to more fully describe the state of the art to which this invention pertains. Full bibliographic information for each citation is found at the end of the specification, immediately following the claims. The disclosures of these references are hereby incorporated by reference into the present disclosure). RSV has also been reported to cause significant morbidity in immunocompromised individuals and the elderly. Globally 65 million infections occur every year resulting in 160,000 deaths (ref. 4). In the USA alone, 100,000 children are hospitalized annually with severe cases of pneumonia and bronchiolitis resulting from an RSV infection (refs. 5, 6). Inpatient and ambulatory care for children with RSV infections has been estimated to cost in excess of $340 million each year in the USA (ref. 7). Severe lower respiratory tract disease due to RSV infection predominantly occurs in infants two to six months of age (ref. 8). The World Health Organization (WHO) and the National Institute of Allergy and Infectious Disease (NIAID) vaccine advisory committees have ranked RSV second only to HIV for vaccine development while the preparation of an efficacious PIV-3 vaccine is ranked in the top ten vaccines considered a priority for vaccine development. Both the annual morbidity and mortality figures as well as the staggering health care costs for managing paramyxoviridae infections including RSV have provided the incentive for aggressively pursuing the development of efficacious RSV vaccines.

RSV is a member of the Paramyxoviridae family of pneumovirus genus (ref. 2). The two major protective antigens of RSV are the envelope fusion (F) and attachment (G) glycoproteins (ref. 9).

In addition to the antibody response generated by the F and G glycoproteins, human cytotoxic T-cells have been shown to recognize the F protein RSV matrix (M) protein, nucleoprotein (N), small hydrophobic protein (SH) and nonstructural protein (1b) (ref. 10), produced following RSV infection. For PIV-3, the protective immunogen are the hemagglutinin-neuramidase (HN) protein and the fusion (F) protein.

Previous attempts to produce a safe and effective RSV vaccine were unsuccessful. Production of live attenuated RSV vaccines has had limited success. The mutants prepared to date have all been either over-attenuated, virulent or genetically unstable. A formalin-inactivated (FI) RSV vaccine developed in the 1960's failed to provide adequate protection in clinical trials (refs. 8, 11, 12). In fact, immunization of seronegative infants with the FI-RSV vaccine resulted in the exacerbation of RSV disease (immunopotentiation) in some vaccinees following exposure to wild type virus. Identification of the major immunoprotective antigens of RSV has provided the scientific rationale for pursuing a subunit approach to RSV vaccine development. However, efficacy of the RSV subunit vaccines tested to date have been inconsistent (ref. 12). There is also conflicting reports in the literature on the ability of an alum-adjuvanted RSV vaccine containing the F protein purified from virus infected cells by immunoaffinity chromatography (PFP-1) to cause enhanced pulmonary pathology (immunopotentiation) following live virus challenge (ref. 13 and 14). There is a definite requirement for the development of a safe and efficacious RSV vaccine.

One of the main obstacles in developing a safe and effective RSV vaccine has been to produce a vaccine formulation that can elicit a protective immune response without causing exacerbated disease. Elucidation of the mechanism(s) involved in the potentiation of RSV disease is important for the design of safe RSV vaccines, especially for the seronegative population. Recent experimental evidence suggests that an imbalance in cell-mediated responses may contribute to immunopotentiation (ref. 15). Enhanced histopathology observed in mice that were immunized with the FI-RSV and challenged with virus could be abrogated by depletion of CD4+ cells or both interleukin-4 (IL-4) and IL-10 (ref. 16). Experimental results indicated that induction of a Th-2 type response may play a role in disease potentiation. BALB/c mice given live virus intranasally or intramuscularly elicited a Th-1 type response, whereas FI-RSV induced a Th-2 type of response. These results were recently substantiated by the finding that BALB/c mice that were immunized with the FI-RSV vaccine had a marked increase in the expression of mRNA (from cells in the bronchoalveolar lavage fluid) for the Th-2 cytokines IL-5 and IL-13 (ref. 17).

Studies on the development of live viral vaccines and glycoprotein subunit vaccines against parainfluenza virus infection are being pursued. Clinical trial results with a formalin-inactivated PIV types 1,2,3 vaccine demonstrated that this vaccine was not efficacious (refs. 33, 34, 35). Further development of chemically-inactivated vaccines was discontinued after clinical trials with a formalin-inactivated RSV vaccine demonstrated that not only as the vaccine not effective in preventing RSV infection but many of the vaccinees who later became infected with RSV suffered a more serious disease. Most of parainfluenza vaccine research has focussed on candidate PIV-3 vaccines (ref. 36) with significantly less work being reported for PIV-1 and PIV-2. Recent approaches to PIV-3 vaccines have included the use of the closely related bovine parainfluenza virus type 3 and the generation of attenuated viruses by cold-adaptation of the virus (refs. 37, 38, 39, 40).

Another approach to parainfluenza virus type 3 vaccine development is a subunit approach focusing on the surface glycoproteins hemagglutinin-neuraminidase (HN) and the fusion (F) protein (refs. 41, 42, 43). The HN antigen, a typical type II glycoprotein, exhibits both haemagglutination and neuraminidase activities and is responsible for the attachment of the virus to sialic acid containing host cell receptors. The type I F glycoprotein mediates fusion of the viral envelope with the cell membrane as well as cell to cell spread of the virus. It has recently been demonstrated that both the HN and F glycoproteins are required for membrane fusion. The F glycoprotein is synthesized as an inactive precursor (F) which is proteolytically cleaved into disulfide-linked F2 and F1 moieties. While the HN and F proteins of PIV-1, 2 and 3 are structurally similar, they are antigenically distinct. Neutralizing antibodies against the HN and F proteins of one PIV type are not cross-protective. Thus, an effective PIV subunit vaccine must contain the HN and F glycoproteins from the three different types of parainfluenza viruses. Antibody to either glycoprotein is neutralizing in vitro. A direct correlation has been observed between the level of neutralizing antibody titres and resistance to PIV-3 infections in infants. Native subunit vaccines for parainfluenza virus type 3 have investigated the protectiveness of the two surface glycoproteins. Typically, the glycoproteins are extracted from virus using non-ionic detergents and further purified using lectin affinity or immunoaffinity chromatographic methods. However, neither of these techniques may be entirely suitable for large scale production of vaccines under all circumstances. In small animal protection models (hamsters and cotton rats), immunization with the glycoproteins was demonstrated to prevent infection with live PIV-3 (refs. 44, 45, 46, 47, 48). The HN and F glycoproteins of PIV-3 have also been produced using recombinant DNA technology. HN and F glycoproteins have been produced in insect cells using the baculovirus expression system and by use of vaccinia virus and adenovirus recombinants (refs. 49, 50, 51, 52, 53). In the baculovirus expression system, both full-length and truncated forms of the PIV-3 glycoproteins as well as a chimeric F-HN fusion protein have been expressed. The recombinant proteins have been demonstrated to be protective in small animal models (see WO91/00104, U.S. patent application Ser. No. 07/773,949 filed Nov. 29, 1991, assigned to the assignee hereof).

The construction of the recombinant poxviruses is described in a number of granted United States patents, including U.S. Pat. Nos. 4,603,112, 4,769,330, 4,722,848 and 5,110,587 relating to various recombinant virus constructs, U.S. Pat. Nos. 5,453,364, 5,225,336 and 5,155,020 relating to attenuated recombinant vaccinia virus constructs and U.S. Pat. No. 5,174,993 relating to recombinant avipox virus constructs. The disclosure of these patens are incorporated herein by reference.

Live recombinant poxviruses expressing the relevant viral proteins may be used alone or as priming immunogens in a prime/boost regime with the subunit vaccine. Despite having promising attributes as a "universal" immunization vehicle, safety issues have provided a concern for the re-introduction of vaccinia virus as an immunizing agent. These concerns stem from complications observed during the Smallpox Eradication Program (ref. 18). From one perspective, the safety issues surrounding the use of vaccinia-based vaccine candidates have been addressed with the development of the NYVAC and ALVAC vectors.

The NYVAC strain was derived from the vaccinia virus Copenhagen strain by the precise deletion of 18 ORFs encoding functions implicated in the pathogenicity of orthopoxviruses, as well as host-range regulatory functions governing the replication competency of these viruses on cells from certain species (ref. 19). General biological properties of NYVAC include: [1] a highly debilitated replicative capacity on cells derived from mice, swine, equids, and humans; [2] the ability to replicate with wildtype efficiency on primary chick embryo fibroblasts, and [3] a highly attenuated phenotype in immunocompetent and immunocompromised animal systems used historically to assess the virulence of vaccinia virus strains (ref. 19). Despite these highly attenuated properties, NYVAC has been shown to function effectively as an immunization vehicle (ref. 19, 20). These properties are consistent with NYVAC providing a safer alternative to existing vaccinia virus vaccine strains for developing vector-based vaccine candidates. Due to the attenuation profile of NYVAC, the Recombinant DNA Advisory Committee of the National Institutes of Health has reduced the biological containment level of this virus from BSL-2 to BSL-1. It is the only member of the Orthopoxvirus genus accorded to a BSL-1 biocontainment level.

The basic vaccinia virus vector technology has been extended to other members of the poxvirus family. Extension to the Avipoxvirus genus, in particular fowlpoxvirus (FPV), was targeted for species-specific applications in the poultry industry (ref. 21). Studies with a FPV recombinant expressing an immunogen from a mammalian pathogen (the rabies virus glycoprotein G), however, demonstrated the ability of this recombinant to elicit immune responses in a number of non-avian species (ref. 22), thus establishing these viruses as viable candidates for developing non-replicating vector-based vaccine candidates for veterinary and human application. The inability of the Avipoxviruses to productively replicate in non-avian species provides an exquisite safety barrier against the occurrence of vaccine-associated and vaccine-induced complications.

Subsequent studies with canarypoxvirus (CPV)-based recombinants in non-avian species also demonstrated their utility as immunization vehicles (refs. 23, 24). In this regard the canarypoxvirus-based recombinants were found superior to similar FPV recombinants and equivalent to thymidine-kinase mutants of replication-competent vaccinia virus recombinants (refs. 19, 24). A plaque-cloned isolate of CPV was derived from the vaccine strain Kanapox and designated ALVAC (ref. 19).

ALVAC, like NYVAC, has demonstrated a highly attenuated phenotype in a number of animal systems comparing existing vaccinia virus vaccine strains (ref. 19). The Recombinant DNA Advisory Committee has reduced the biological containment for ALVAC to BSL-1. Furthermore, ALVAC has been shown to be an effective immunization vehicle in a number of non-avian species including humans (ref. 25). The concept of using a non-replicating vector in humans was supported by the results of phase I clinical trials using an ALVAC-based rabies G (ref. 26) and an ALVAC-HIV-1$_{MN}$ env (ref. 27) recombinant. In each study, the ALVAC-based recombinant elicited antigen-specific immune responses the heterologous antigen. Thus, the use of either ALVAC or NYVAC recombinants expressing the pertinent RSV proteins represents a promising approach for RSV vaccine development.

SUMMARY OF THE INVENTION

The present invention provide a novel immunization strategy to provide protection against disease caused by infection and members of the Paramyxoviridae family, particularly respiratory syncytial virus (RSV) and parainfluenza virus (PIV). The immunization strategy provided herein leads to a stronger protective immune response than other strategies.

According to one aspect of the invention, there is provided a method of immunizing a host against disease caused by infection by a paramyxoviridae viruses, which comprises:

initially administering to the host an immunoeffective amount of a recombinant virus expressing at least one paramyxoviridae virus protein or immunogenic fragment thereof, and subsequently administering to the host an immunoeffective amount of at least one purified paramyxoviridae protein or immunogenic fragment thereof the same at least one paramyxoviridae protein as used in the initial administration, to achieve a paramyxovirus specific protective immune response in the host.

The immune response which is achieved in the host by the method of the invention preferably includes the production of virus specific neutralizing antibodies and virus specific cytotoxic T-cell response. The immunization strategy employed herein may lead to the induction of a more balanced Th-1/Th-2 response than previously attained.

While the invention is broadly effective with members of the paramyxoviridae family, the invention is preferably effective to provide protection against respiratory tract diseases caused by respiratory syncytial virus (RSV) and parainfluenza virus (PIV), in particular respiratory syncytial virus.

The recombinant virus may express at least one of the F, G and M proteins of RSV or an immunogenic fragment thereof, particularly the F glycoprotein of RSV.

The purified RSV protein or immunogenic fragment thereof employed in the second or booster administration may be selected from the group consisting of the F, G, and M proteins of RSV or immunogenic fragments thereof and may compris a mixture of two or three of these RSV proteins or the immunogenic fragments thereof.

The at least one purified paramyxoviridae protein or immunogenic fragment thereof, including mixtures of the F, G and/or M proteins or RSV or immunogenic fragments thereof, may be administered with an adjuvant or immunomodulator including alum.

In a further aspect of the present invention, there is provided a novel recombinant poxvirus containing therein a nucleic acid sequence encoding a paramyxoviridae protein or immunogenic fragment thereof in a non-essential region of the recombinant virus genome.

The poxvirus may be a vaccinia virus, in particular one in which non-essential virus-encoded genetic functions have been inactivated therein so as to provide an attenuated vaccinia virus. In one embodiment, such attenuated vaccinia virus may contain a nucleic acid sequence encoding the F glycoprotein of respiratory syncytial virus (RSV). One such recombinant vaccinia virus is provided herein and is designated virus vP1000 (NYVAC-F) having the ATCC Deposit No. VR-2540.

Alternatively, the poxvirus may be an avipox virus, which may be a fowlpox virus, which is non-virulent in humans. In one embodiment, the nucleic acid sequence encodes the F glycoprotein of respiratory syncytial virus (RSV). One such recombinant avipox virus is provided herein and is designated virus vCP181 (ALVAC-F) having ATCC Deposit No. VR-2541.

The present invention further comprises the use of such recombinant poxvirus as a medicine or in the manufacture of a medicament.

BRIEF DESCRIPTION OF DRAWINGS

FIG. 1, containing panels a and b, shows SDS-PAGE analysis of a purified RSV subunit preparation using acrylamide gels stained with silver, under both reduced (panel (a)) and non-reduced (panel (b)) conditions;

FIG. 2, containing panels a, b, c and d, shows Western blot analysis of a purified RSV subunit preparation under reduced conditions;

FIG. 3, containing panels a, b, c and d, shows Western blot analysis of a purified RSV subunit preparation under non-reduced conditions;

FIG. 4 shows the nucleotide sequence of the recombinant pox virus vCP181 (SEQ ID No. 21) or (ALVAC-F), an H6-promoted RSV-F gene insertion with flanking sequences. The H6 promoter commences at position 202 and the RSV-F gene starts at position 326 and ends at position 2048;

FIG. 5 shows the nucleotide sequence of the recombinant poxvirus virus vP1000 (SEQ ID No: 22) (NYVAC-F), an H6 promoted RSV-F gene insertion with flanking sequences. The H6 promoter begins at position 575. The RSV-F gene starts at position 699 and ends at position 2421;

GENERAL DESCRIPTION OF THE INVENTION

The present invention relates to methods of immunization comprising administration of a recombinant virus expressing at least one paramyxoviridae virus protein or immunogenic fragment thereof and subsequent administration of at least one protein or fragment thereof of the same protein of the paramyxoviridae virus.

The recombinant virus vector expressing at least one paramyxoviridae virus protein may itself be unable to confer protection.

In one aspect, the at least one protein may comprise a mixture of RSV proteins such as G glycoprotein, F glycoprotein, M protein and heterodimers and oligomeric forms of the G and G proteins. Thus, the subsequent administration may be of a subunit preparation isolated from RSV viral concentrates. Referring to FIGS. 1 to 3, there is shown an analysis of a composition of the RSV subunit preparation by SDS-PAGE analysis (FIG. 1) and Western blot (FIGS. 2 and 3). A typical composition of the RSV subunit preparation determined by densitometric scanning is:

| | |
|---|---|
| G glycoprotein (95 kDa form) | 10% |
| $F_1$ glycoprotein (48 kDa) | 30% |
| M protein (31 kDa) | 23% |
| $F_2$ glycoprotein (23 kDa) | 19% | when analyzed under reducing conditions by SDS-PAGE and silver staining.

As described above the primary (priming) immunization may be by administration of a recombinant virus expressing at least one paramyxoviridae virus protein. The recombinant virus may be a pox virus modified to contain a gene encoding at least a portion of the paramyxoviridae virus protein such as the RSV F protein. The poxvirus may be attenuated for the usually mammalian host by modification of regions of the poxvirus genome necessary for virulence to produce, for example, a NYVAC-F recombinant virus such as vP1000. In an alternative embodiment, the poxvirus may be virus such as an avipox virus that does not replicate in mammalian hosts. Such a recombinant virus is ALVAC-F, such as vCP181.

Figure 6A:
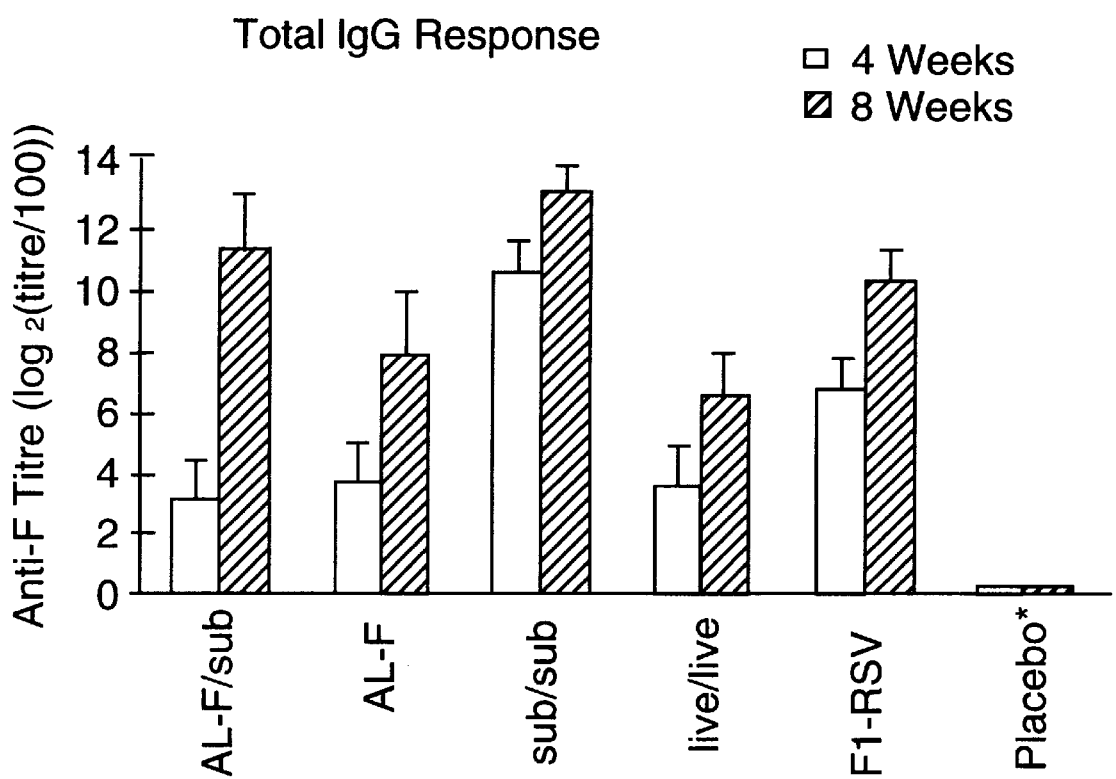
FIG. 6, containing panels A, B and C, shows the anti-RSV F antibody titres in the sera of mice immunized with different prime/boost protocols, as detailed in Table 1 below.
Figure 6B:
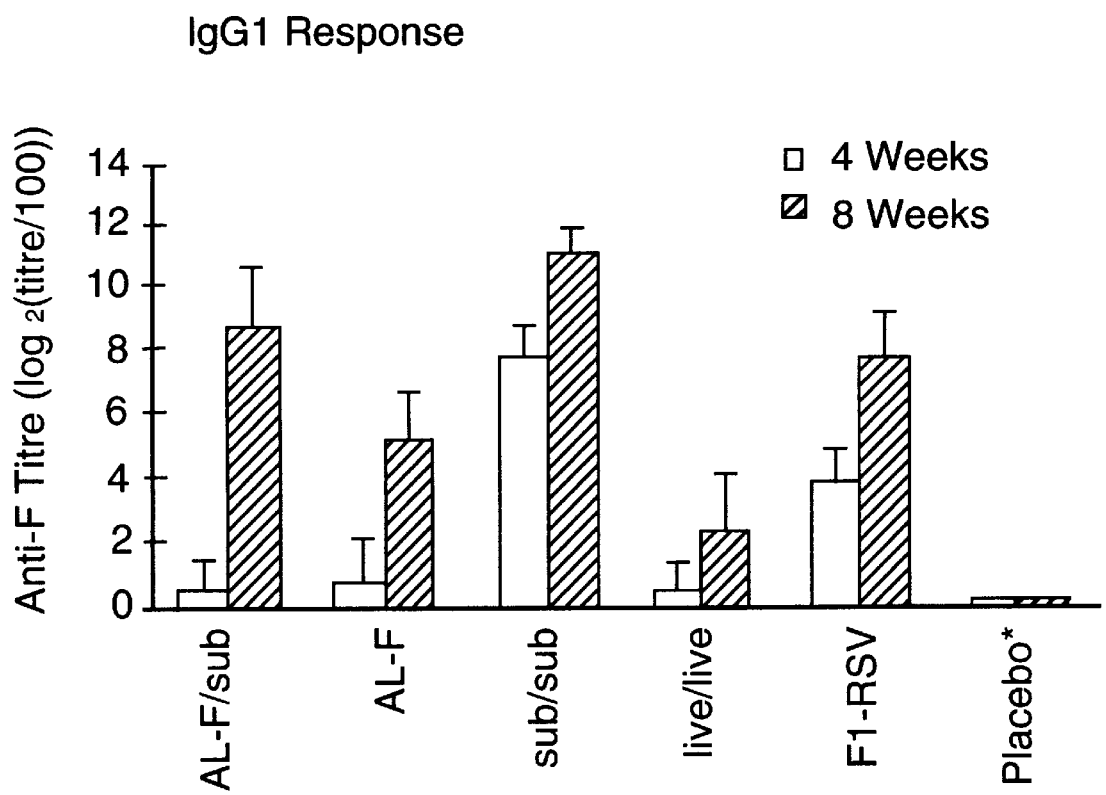
Figure 6C:
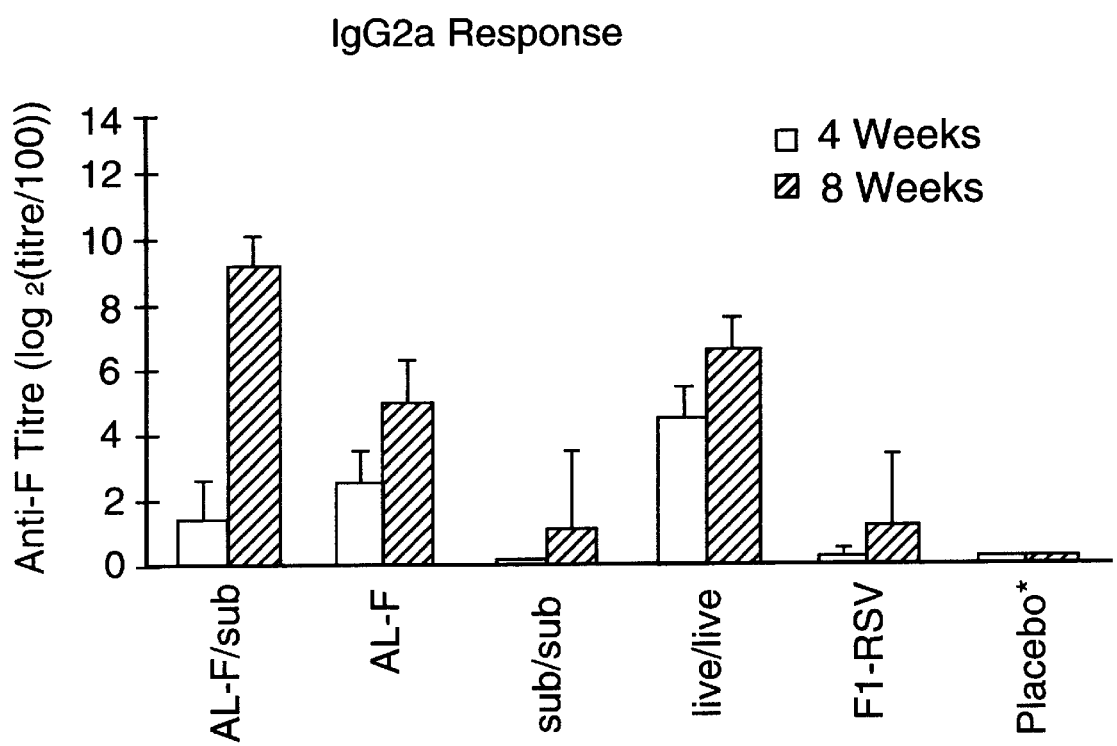
Figure 7:
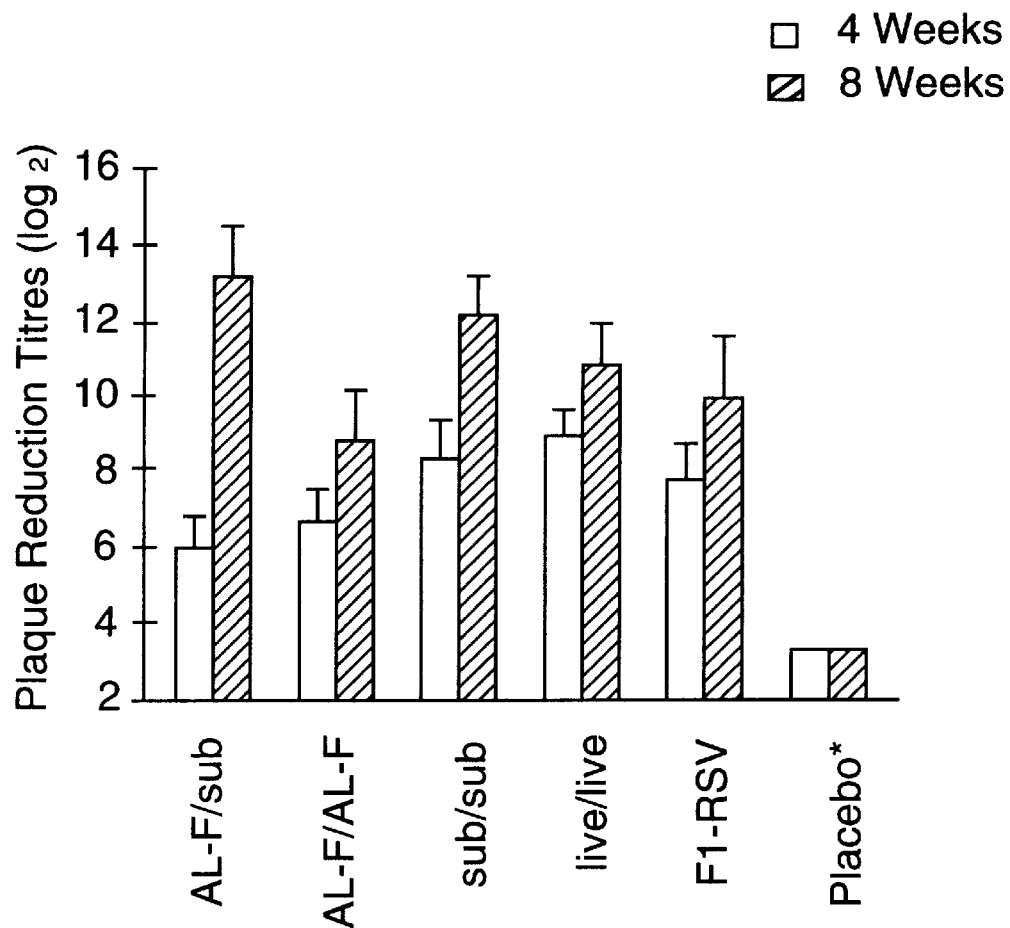
FIG. 7 shows the plaque reduction titres in the sera of mice immunized with different prime/boost protocols, as detailed in Table 1 below.
Figure 8:
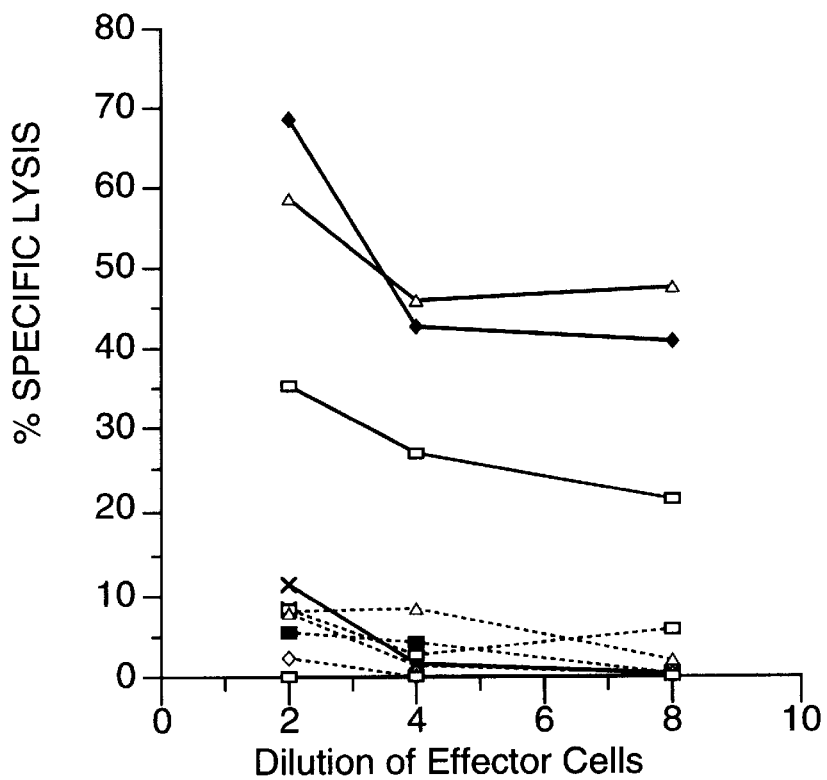
FIG. 8 shows the cytotoxic T lymphocyte responses in mice immunized with different prime/boost protocols, as detailed in Table 1 below.

Recombinant avipox viruses containing the gene encoding the F protein of RSV were constructed and used to immunize mice as shown in Table 1. Total anti-F IgG, IgG1 and IgG2 antibodies were measured in murine sera and the results are shown in FIG. 6. The sera from animals that were primed with the ALVAC-F recombinant virus and boosted either with the ALVAC-F recombinant virus or the subunit preparation had anti-F IgG1/IgG2a ratios of approximately 1:1. This is in contrast to the anti-RSV F IgG1/IgG2a ratios obtained in mice that were primed and boosted with formalin-inactivated RSV (8:1) or subunit vaccine (11:1). The induction of IgG2A in mice is indicative of a Th1 immune response. The sera of mice primed with the ALVAC-F recombinant virus and boosted with the RSV proteins as a subunit preparation contained high levels of virus neutralizing antibodies as shown by plaque reduction titres (FIG. 7). Mice primed with the poxvirus recombinant and then boosted with RSV proteins produced RSV-specific cytotoxic T cells as shown in FIG. 8. Of significance is that mice primed with recombinant pox expressing the RSV F protein and boosted with RSV proteins were protected from challenge with live RSV as shown in Table 2. In particular, mice primed and boosted with ALVAC-F recombinant virus had detectable virus in their lungs whilst no virus could be detected in the lungs of mice that were primed with ALVAC-F and boosted with RSV proteins or an RSV subunit preparation.

The invention extends to the use of a recombinant virus expressing at least one paramyxoviridae virus protein for primary immunization (priming) of a host and the subsequent use of at least one paramyxoviridae virus protein for boosting said host to protect said host against disease caused by paramyxoviridae.

The vaccines are administered in a manner compatible with the dosage formulation, and in such amount as will be therapeutically effective, immunogenic and protective. The quantity to be administered depends on the subject to be treated, including, for example, the capacity of the immune system of the individual to synthesize antibodies, and, if needed, to produce a cell-mediate immune response. Precise amounts of active ingredient required to be administered depend on the judgment of the practitioner. However, suitable dosage ranges are readily determinable by one skilled in the art and may be of the order of micrograms to milligrams of the proteins or fragments thereof and $10^5$–$10^9$ pfu of the combinant virus. The dosage may also depend on the route of administration and will vary according to the size of the host.

Immunogenicity can be significantly improved if the antigens are co-administered with adjuvants. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and, more recently, a HBsAg vaccine has been adjuvanted with alum. While the usefulness of alum is well established for some applications, it has limitations. For example, alum is ineffective for influenza vaccination and usually does not elicit a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include aluminum phosphate, aluminum hydroxide, QS21, Quil A, derivatives and components thereof, calcium phosphate, calcium hydroxide, zinc hydroxide, a glycolipid analog, an octodecyl ester of an amino acid, a muramyl dipeptide, polyphosphazene, a lipoprotein, ISCOM matrix, DC-Chol, DDA, and other adjuvants and bacterial toxins, components and derivatives thereof as, for example, described in U.S. application Ser. No. 08/481,878, assigned to the assignee hereof and the disclosure of which is incorporated herein by reference thereto. Under particular circumstances adjuvants that induce a Th1 response are desirable.

The at least one purified paramyxovirus protein or immunogenic fragment thereof used in the booster administration may be provided in any convenient manner. For example, the protein, proteins or immunogenic fragments may be extracted from cellular material, such as by detergent extraction, and may be purified by affinity chromatography, as described, for example, in WO 91/00104, assigned to the assignee hereof and the disclosure of which is incorporated herein by reference. Alternatively, an immunoaffinity purification procedure may be used.

Alternatively, the protein, proteins or immunogenic fragments thereof may be prepared recombinantly by expression of the protein or fragment thereof from a suitable vector with subsequent purification of the expressed material. Suitable vectors and expression systems are described, for example, in WO 87/04185.

In general, plasmid vectors containing replicon and control sequences which are derived from species compatible with the host cell may be used for the expression of the relevant genes in expression systems. The vector ordinarily carries a replication site, as well as marking sequences which are capable of providing phenotypic selection in transformed cells. Details concerning the nucleotide sequences of promoters are known, enabling a skilled worker to ligate them functionally with the relevant genes. The particular promoter used will generally be a matter of choice depending upon the desired results. Hosts that are appropriate for expression of the relevant genes and immunogenic fragments thereof include bacteria, eukaryotic cells, fungi, yeast or the baculovirus expression system may be used.

It may be preferred to make the relevant protein or immunogenic fragment thereof, particularly when the naturally occurring protein as purified from a culture may include trace amounts of toxic materials or other contaminants. This problem may be avoided by using recombinantly produced protein in heterologous systems which can be isolated from the host in a manner to minimize contaminants in the purified material.

Biological Deposits

Certain recombinant pox viruses that are described and referred to herein have been deposited with the American Type Culture Collection (ATCC) located at 12301 Parklawn Drive, Rockville, Md. 20852, USA pursuant to the Budapest Treaty and prior to the filing of this application. Samples of the deposited viruses will become available to the public ad all restrictions imposed on access to the deposits will be removed upon grant of a patent on this application. The invention described and claimed herein is not to be limited in scope by recombinant viruses deposited, since the deposited embodiment is intended only as an illustration of the invention. Any equivalent of similar recombinant virus are within the scope of the invention.

Deposit Summary

| Recombinant Virus | ATCC Designation | Date Deposited |
|---|---|---|
| vP1000 (NYVAC-F) | VR-2540 | July 12, 1996 |
| cVP181 (ALVAC-F) | VR-2541 | July 12, 1996 |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Example 1

This Example describes the generation of the ALVAC recombinant containing the RSV-F gene.

Plasmid pSKF7, containing the coding sequence for the RSV type A fusion glycoprotein (RSV-F), was obtained from Institute Merieux, Lyon, France. RSV-F coding sequences, from plasmid pSKF7, were placed under control of a vaccinia virus promoter by joining fragments which had been amplified by the polymerase chain reaction (PCR) (ref. 28). The modified vaccinia virus early/late H6 promoter (ref. 29), followed by the 5' base pairs of the RSV F gene, was amplified by PCR from plasmid pRW825 containing the H6 promoter sequence oligonucleotide primers RW325 (SEQ ID No: 1) (5'-GATTGAGGATCCTTAATTAATTAGTGATAC-3') and RW326 (SEQ ID No: 2) (5'-TGCATTTGCTT TGAGGATTAGCAACTCCATTACGATACAAACTTA-3') were used in a PCR, with plasmid template pRW825, to generate a 200 bp H6 promoter fragment with the translation initiation codon of the H6 promoter overlapping the RSV F translation initiation codon. Oligonucleotide RW325 contains a BamHI site followed by a sequence which primes 5' of the H6 promoter toward the H6 promoter 3' base pairs. Oligonucleotide primer RW326 contains the 5' base pairs of RSV F followed by a sequence which primes from the H6 translation initiation codon toward the H6 promoter 5' base pairs.

Oligonucleotide RW327 (SEQ ID No: 3) (5'-ATGGAGTTGCTAATCCTC-3') primes from the RSV-F gene translation initiation codon toward the RSV-F 3' end of the RSV F gene encoding sequence. Oligonucleotide RW328 (SEQ ID No: 4) (5'-GGGAATACTAATGGGCTTGATATTACTTAATTC-3') primes from the RSV-F gene codon 65 toward the RSV-F 5' base pairs. Template plasmid pSKF7 was used in a PCR with the oligonucleotide primers RW327 and RW328, yielding a 220 bp fragment containing the 5' base pairs of RSV F gene. The 3' base pairs of the PCR fragment derived with RW327 and RW328 overlaps the 5' base pairs of the following PCR fragment derived with the oligonucleotide primers RW329 and RW330.

The 5' base pairs of oligonucleotide RW329 (SEQ ID No: 5) (5'-TTAAGTAATATCAAGCCCATTAGTATTCCCCTC-3') contains the reverse complement of RW328 followed by a sequence which primes toward the RSV F gene 3' base pairs. The 5' base pairs of oligonucleotide RW330 (SEQ ID No: 6) (5'-GGTACTTGGAAGCTTTCAGTTACTAAATGCAAT-3') contains a HindIII site, followed by a sequence which primes from the RSV-F stop codon toward the RSV F gene 5' base pairs. Oligonucleotide primers RW329 and RW330 were used in a PCR with the template pSKF7. The 5' base pairs of the resultant 330 bp RW329/RW330 PCR amplified fragment overlaps the 3' base pairs of the RW327/RW328 PCR product, followed by the 3' base pairs of RSV F gene.

The three overlapping PCR products derived with the primer pairs RW325/RW326, RW327/RW328, and RW329/RW330 were pooled and used as a PCR template with the primers RW325 and RW330. The resultant PCR, amplified with the primers RW325/RW330, fused the three template fragments into one fragment containing the H6 promoted 5' base pairs of the RSV F gene followed by the 3' base pairs of RSV-F gene. Addition of the central RSV-F coding sequences is described below. The RW325/RW330 PCR fragment was digested with NruI (with the H6 promoter) and HindIII (3' of RSV-F gene) for insertion between the NruI and HindIII sites of the H6 promoter vector pRW880. The resultant plasmid, pRW884, contains the H6 promoted RSV F gene 5' base pairs followed by the 3' base pairs. The following RW358/RW330 PCR amplified fragment was used to add the central RSV-F coding sequences to pRW884.

The poxvirus early transcription termination signal TTTTTNT (ref. 30) was altered within the RSV-F gene coding sequence, without changing the amino acid coding sequence, with a PCR fragment amplified with the oligonucleotide primers RW358/RW330. The RW358/RW330 PCR fragment was derived from two overlapping PCR fragments in the following manner.

The RSV-F gene central coding sequence contains a poxvirus early transcription termination signal. The TTTTTNT sequence was inactivated by base substitution which did not change the amino acid sequence but will prevent early transcriptional termination in a poxvirus vector. Plasmid pRW884 was designed for insertion of the RSV-F central coding sequence, with an inactivated TTTTTNT, as a SpeI-NdeI fragment. Poor efficiency of pRW884 digestion with NdeI resulted in a change of strategy from the SpeI-NdeI fragment to utilization of the following SpeI-HindIII fragment.

Oligonucleotides RW356 (SEQ ID No: 7) (5'-AGATTTCTTGGTTTCCTGTTAGGTGTTGGATC-3') and RW330 (SEQ ID No: 6) (5'-GGTACTTGGAAGCTTTCAGTTACTAAATGCAAT-3') primed plasmid template pSKF7 for PCR. The 5' base pairs of RW356 contains the poxvirus early transcription termination signal sequence TTTTTGT, which has been inactivated by alternation to TTCCTGT, followed by a sequence which primes toward the RSV F gene 3' most base pairs.

RW330 contains a HindIII site followed by a sequence which primes from the RSV-F gene stop codon toward the RSV F 5' base pairs. The resultant 1.3 kbp RW356/RW330 PCR amplified fragment contains the 3' base pairs of RSV F gene; the 5' end of the fragment overlaps the 3' end of the following RW357/RW358 PCR amplified fragment.

Oligonucleotides RW358 (SEQ ID No: 8) (5'-TCTTAGTGCTCTAAGAAC-3') and RW357 (SEQ ID No: 9) (5'-TCCAACACCTAACAGGAAACCAAGAAATCTTC-3') primed plasmid template pSKF7 for PCR, yielding a 300 bp fragment. The 5' base pairs of RW357 contains the reverse complement of the altered poxvirus early transcription termination signal followed by a sequence which primes toward the 5' most base pairs of RSV F gene. Oligonucleotide RW358 primes from the 5' base pairs of RSV F gene toward the 3' base pairs of RSV-F gene.

The two overlapping PCR products amplified with the primer pairs RW356/RW330 or RW357/RW358 were pooled and used as a PCR template with the primers RW358 and RW330. The resultant 1.6 kbp RW358/RW330 amplified fragment, containing the 3' base pairs of RSV F gene and an inactivated poxvirus early transcription termination signal, was digested with SpeI and HindIII, yielding a 1.56 kbp fragment. The 1.56 kbp SpeI/HindIII digested RW358/RW330 PCR amplified fragment was inserted between the SpeI and HindIII sites of pRW884. The resultant plasmid pRW887 contains the H6 promoted RSV-F gene open reading frame flanked by NotI restriction sties.

Plasmid pC6L was used as a vector for the H6 promoted RSV-F gene from pRW887. Plasmid pC6L was constructed by deleting the C6 ORF and replacing it with multiple cloning sites flanked by transcriptional and translational termination signals in the following manner. A 380 bp PCR fragment was amplified from genomic ALVAC DNA using oligonucleotide primers C6A1 (SEQ ID No: 10) (5'-ATCATCGAGCTCGCGG CCGCCTATCAAAAGTCTTAATGAGTT-3') and C6B1 (SEQ ID No: 11) (5'-GAATTCCTCGAGCTGCAGCCCGGGTTTT-TATAGCTAATTAGTCATTTTTTCGTAA GTAAGTATTTTTATTTAA-3'). A 1155 bp PCR fragment was amplified from genomic ALVAC DNA using oligonucleotide primers C6C1 (SEQ ID No: 12) (5'-CCCGGGCTGCAGCTCGAGGAATTCTTTT-TATTGATTAACTAGTCAAATGAGTATA TATAATTGAAAAAGTAA-3') and C6D1 (SEQ ID No: 13) (5'-GATGATGGTACCTTCAT AAATACAAGTTTGATTAAACTTAAGTTG-3'). The 380 bp and 1155 bp fragments were fused by adding them together as a template and amplifying a 1613 bp PCR fragment using oligonucleotide primers C6A1 and C6D1. This fragment was digested with SacI/KpnI and ligated into pBluescript SK+ digested with SacI/KpnI. The resulting plasmid, pC6L was confirmed by DNA sequence analysis. It consists of 370 bp of ALVAC DNA upstream of C6, vaccinia early termination signal, translation stop codons in six reading frames, multiple cloning sites containing SmaI, PstI, XhoI and EcoRI sites, vaccinia early termination signal, translation stop codons in six reading frames and 1156 bp of downstream ALVAC sequence.

The 1.9 kbp pRW887 NotI fragment, containing the H6 promoted RSV-F gene expression cassette, was blunt ended with Klenow DNA polymerase in the presence of 20 mM dNTPs and inserted into the SmaI site of the ALVAC C6 donor plasmid pC6L. The resultant plasmid pRW927 contains the H6 promoted RSV-F open reading frame in a C6 donor plasmid. Plasmid pRW927 was used in in vitro recombination experiments with ALVAC as the rescuing virus to yield vCP181.

EXAMPLE 2

This Example describes the construction of the NYVAC recombinant containing the RSV-F gene.

The H6 promoted RSV-F gene expression cassette was moved into the NYVAC donor plasmid pSD544. Plasmid pSD544 was constructed in the following manner. pSD456 is subclone of Copenhagen vaccinia DNA containing the HA gene (ref. 31) and surrounding regions. pSD456 was used as a template in PCR for synthesis of left and right vaccinia arms flanking the A56R ORF. The left arm was synthesized using oligonucleotides MPSYN279 (SEQ ID No: 14) (5'-CCCCCCGAATTCGTCGAC GATTGTTCATGATGGCAAGAT-3') and MPSYN280 (SEQ ID No: 15) (5'-CCCGGGGGATCCCTCGAGGGTAC-CAAGCTTAATTAATTAAATATTAGTATAAAAA GTGATTTATTTTT-3'). The right arm was synthesized using oligonucleotides MPSYN281 (SEQ ID No: 16) (5'-AAGCTTGGTACCCTCGAGGGATC-CCCCGGGTAGCTAGCTAATTTTTCTTTTACGT ATTATA TATGTAATAAACGTTC-3') and MPSYN312 (SEQ ID No: 17) (5'-TTTTTT CTGCAGGTAAGTATTTTTAAAACTTCTAACACC-3'). The purified PCR fragments for the left and right arms were combined in a further PCR reaction. The resulting product was digested with EcoRI/HindIII. The resulting 0.9 kb fragment was cloned into EcoRI/HindIII digested pUC6 resulting in plasmid pSD544.

The previously described 1.9 kbp pRW887 NotI fragment, containing the H6 promoted RSV F gene expression cassette, was blunt ended with Klenow DNA polymerase in the presence of 20 mM dNTPs and inserted into the SmaI site of the vaccinia virus HA donor plasmid pSD544. The resultant plasmid pRW891 contains the H6 promoted RSV-F gene open reading frame in an HA donor plasmid. Plasmid pRW891 was used in in vitro recombination experiments with NYVAC as the rescuing virus to yield vP1000.

EXAMPLE 3

This Example describes the expression analysis of vCP181 (ALVAC-F recombinant virus) and vP1000 (NYVAC-F recombinant virus).

Immunoprecipitation analysis was performed to assay RSV-F expression in vCP181 (ALVAC-F) and vP1000 (NYVAC-F) infected cells. Authentic RSV-F is expressed as an $F_0$ (68–70 kDa) precursor which is cleaved, yielding the products $F_1$ (46 kDa) and $F_2$ (22 kDa). Polypeptide species corresponding to proteins with molecular weights consistent with $F_0$, $F_1$, and $F_2$ in lysates derived from vCP181 and vP1000 infected cells were detected using rabbit anti-RSV antiserum.

More specifically, HeLa, MRC-5, or CEF cells were labelled with 20–50 $\mu$Ci/ml $^{35}S$ methionine (NEN, Boston, Mass) and infected with recombinant or control virus at an MOI of 10. Rabbit anti-RSV F antiserum (Paster Merieux, 46-3-S9 du 30.08.89), was used in immunoprecipitations at dilutions of 1:10 to 1:100. Negligible reactivity was obtained, at molecular weights consistent with $F_0$, $F_1$, and $F_2$, from cells infected with the control viruses ALVAC or NYVAC. Both vCP181 (ALVAC-F) and vP1000 (NYVAC-F) were positive for RSV-F expression. The vCP181 or vP1000 infected cells yielded antigens of the appropriate sizes for RSV-$F_0$, $F_1$, and $F_2$.

EXAMPLE 4

This Example illustrates the process of purifying RSV proteins.

African Queen monkey kidney cells (VERO) at a concentration of $10^5$ cells/mL were added to 60L of CMRL 1969 medium, pH 7.2 in a 150L bioreactor containing 360 g of Cytodex-1 microcarrier beads and stirred for 2 hours. An additional 60L of CMRL 1969 was added to give a total volume of 120L. Fetal bovine serum was added to achieve a final concentration of 3.5%. Glucose was added to a final concentration of 3 g/L and L-glutamine was added to a final concentration of 0.6 g/L. Dissolved oxygen (40%), pH (7.2), agitation (36 rpm), and temperature (37° C.) were controlled. Cell growth, glucose, lactate, and glutamine levels were monitored. At day 4, the culture medium was drained from the fermenter and 100L of E199 media (without fetal bovine serum) was added and stirred for 10 minutes. The fermenter was drained and filled again with 120 L of E199. The RSV inoculum was added at a multiplicity of infection (M.O.I.) of 0.001 and the culture was then maintained for 3 days before one-third to one-half of the media was drained and replaced with fresh media. On day 6 post-infection the stirring was stopped and the beads allowed to settle. The viral culture fluid was drained and filtered through a 20 µm filter followed by a 3 µm filter prior to further processing. The clarified viral harvest was concentrated 75–100 fold using tangential flow ultrafiltration with 300 NMWL membrane and diafiltered with phosphate buffered saline containing 10% glycerol. The viral concentrate was stored frozen at –70° C. prior to further purification. A solution of 50% polyethylene glycol-8000 was added to an aliquot of virus concentrate to give a final concentration of 6%. After stirring at room temperature for one hour, the mixture was centrifuged at 15,000 RPM for 30 min. in a Sorvall SS-34 rotor at 4° C. In some instances the viral pellet was suspended in 1 mM sodium phosphate, pH 6.8, 2 M urea, 0.15 M NaCl, stirred for 1 hour at room temperature, and then recentrifuged at 15,000 RPM for 30 min. in a Sorvall SS-34 rotor at 4° C. The viral pellet was then suspended in 1 mM sodium phosphate, pH 6.8, 50 mM NaCl, 1% Triton X-100 and stirred for 30 min. at room temperature. The insoluble virus core was removed by centrifugation at 15,000 RPM for 30 min. in a Sorval SS-34 rotor at 4° C. The soluble protein supernatant was applied to a column of ceramic hydroxyapatite (type II, Bio-Rad Laboratories) and the column was then washed with five column volumes of 2 mM sodium phosphate, pH 6.8, 30 mM NaCl, 0.02% Triton X-100. The RSV proteins were obtained by eluting the column with 10 column volumes of 1 mM sodium phosphate, pH 6.8, 400 mM NaCl, 0.02% Triton X-100.

The RSV proteins were analyzed by SDS-PAGE using 12.5% acrylamide gels and by immunoblotting. Samples were electrophoresed in the presence or absence of the reducing agent 2-mercaptoethanol. Gels were stained with silver stain to detect the viral proteins (FIGS. 1a and 1b). Immunoblots of replicate gels were prepared and probed with a mouse monoclonal antibody (mAb 5353C75) to F glycoprotein (FIGS. 2a and 3a), or a mouse monoclonal antibody (mAb 131-2G), to G glycoprotein (FIGS. 2b and 3b) or guinea pig anti-serum (gp178) against an RSV M peptide (peptide sequence: LKSKNMLTTVKDLTMKTLNPTHDIIALCEFEN-SEQ ID No: 20) (FIGS. 2c and 3c), or goat anti-serum (Virostat #0605) against whole RSV (FIGS. 2d and 3d). Densitometric analysis of the silver-stained gel of RSV subunit preparation electrophoresed under reducing conditions indicated a compositional distribution as follows:

G glycoprotein (95 kDa form)=10%
$F_1$ glycoprotein (48 kDa)=30%
M protein (31 kDa)=23%
$F_2$ glycoprotein (23 kDa)=19%

The F glycoprotein migrates under non-reducing conditions as a heterodimer of approximately 70 kDa ($F_0$) as well as higher oligomeric forms (dimers and trimers) (FIG. 3a).

EXAMPLE 5

This example describes the immunization of animals by priming with the ALVAC-F recombinant virus and boosting with RSV proteins.

Pathogen-free BALB/c mice (approximately 8 weeks old; 17 animals per group) were immunized according to the immunization protocol outlined in Table 1.

Animals were bled 4 weeks after the primary inoculation and boosted with the vaccine formulation outlined in Table 1. Serum samples were also taken 4 weeks after the booster does. The anti-RSV F antibody titres in the sera of mice that were immunized according to the protocol outlined in Table 1 are summarized in FIG. 6. With the exception of the control animals, the sera of mice immunized with the various RSV formulations contained had anti-F IgG antibodies. The sera from animals that were primed with the ALVAC-F recombinant virus and boosted with either the ALVAC-F recombinant virus or the subunit preparation had anti-F IgG1/IgG2a ratios of approximately 1:1. This is in contrast to the anti-RSV F IgG1/IgG2a ratios obtained in mice that were primed and boosted with the alum-adjuvanted FI-RSV (8:1) or subunit vaccine (11:1). These results indicate that priming animals with the ALVAC-F recombinant virus results in a balanced anti-RSV F IgG1/IgG2a response and sets the stage for a Th-1 type response.

As shown in FIG. 7, the sera of mice that were primed and boosted with the various RSV preparations outlined in Table 1, all had significant levels of RSV-specific neutralizing antibodies. The RSV-specific neutralizing antibody titers (13 $log_2$) were significantly higher in animals that were primed with the ALVAC-F recombinant and boosted with the subunit preparation than in mice that were primed and boosted with the ALVAC-F recombinant virus (neutralizing antibody titre 8.8 $log_2$). Thus, priming animals with the ALVAC-F recombinant virus not only appears sets the stage for a Th-1 type response but also results in the induction of high titres of RSV-specific neutralizing antibodies after boosting with the alum-adjuvanted RSV subunit vaccine.

EXAMPLE 6

This Example describes the determination of Anti-F antibody titres

Nunc-MaxiSorp plate wells were coated overnight at room temperature with 2.5 ng of immunoaffinity-purified RSV-F protein diluted in 0.05M carbonate-bicarbonate buffer, pH9.6. Wells were blocked for non-specific binding by adding 0.1% BSA in PBS for 30 min. at room temperature, followed by two washes in a washing buffer of 0.1% BSA in PBS+0.1% Tween 20. Serial two or four-fold dilutions of mouse serum was added to the wells. After one hour incubation at room temperature, plates were washed five times with washing buffer, and horseradish peroxidase (HRP) labelled conjugate was added at the appropriate optimal dilution in washing buffer. The total IgG assay was used F(ab')$_2$ goat anti-mouse IgG (H+L specific)-HRP from Jackson Immuno Research Laboratory Inc., Baltimore, Md. Sheep anti-mouse IgG1-HRP from Serotec, Toronto, Ontario was used in the IgG1 assay and goat anti-mouse IgG2a from Caltag Laboratories, San Francisco, Calif. was used in the IgG2a assay. Following one hour incubation at room temperature, the plates were washed five times with washing buffer, and hydrogen peroxide (substrate) in the presence of tetramethylbenzidine was added. The reaction was stopped by adding 2 M sulfuric acid. The colour was read in a Multiscan Titertek plate reader at an optical density (OD) of 450 nm. The titre was taken as the reciprocal of the last dilution at which the OD was approximately double. This OD must be greater that the negative control of the assay at the starting dilution. The pre-immune serum of each animal was used as the negative control.

EXAMPLE 7

This Example describes the generation of RSV-specific cytotoxic T-cells in mice primed with live recombinant poxvirus and boosted with RSV proteins.

Spleens from two BALB/c mice from each group that were immunized according to the immunization protocol outlined in Table 1 were removed three weeks after the booster dose. Single cell suspensions were prepared and incubated at $2.5 \times 10^7$ cell in RPMI 1640 plus 10% fetal bovine serum (FBS). Gamma-irradiated (3,000 rads) syngeneic spleen cells were infected with RSV at an MOI of 1 for 2 hours. The cells were washed twice to remove free virus and $2.5 \times 10^7$ virus infected feeder cells were added to the $2.5 \times 10^7$ spleen cells in a final volume of 10 mL of complete medium. CTL activity was tested 5 to 6 days following re-stimulation. On the day of the assay, effector cells were washed twice with fresh medium and viable cell counts were determined by the Trypan blue dye exclusion method. BC cells ($2 \times 10^6$ cells), a BALB/c fibroblast cell line, as well as BCH4 cells ($2 \times 10^6$ cells), a BALB/c fibroblast T cell line persistently infected with RSV, were pulsed with 200 µCi of Sodium $^{51}$chromate (Dupont) for 90 min. The targets were washed three times with medium to remove free $^{51}$chromium. Viable cell counts of the target cells were determined and target cell suspensions were prepared at $2 \times 10^4$ cells/mL. Washed responder T-cells (in 100 µL) were incubated with $2 \times 10^3$ target cells (in 100 µL) at varying Effector:Target cell ratios in triplicates in a 96-well V-bottomed tissue-culture plates for 4 hours at 37° C. with 6% $CO_2$. Spontaneous and total release of $^{51}$chromium were determined by incubating target cells with either medium or 2.5% Triton X-100 in the absence of responder lymphocytes, respectively. Six replicates of each were prepared. After 4 hours, plates were centrifuged at 200×g for 2 min and 100 µL of supernatant were removed from each well to determine the amount of $^{l}$chromium released. Percentage specific $^{51}$chromium release was calculated as (Experimental Release−Spontaneous Release)/(Total Release−Spontaneous Release)×100. The Spontaneous Release of $^{51}$chromium in the absence of effector cells was found to be between 10 to 15% in these studies.

As shown in FIG. 8, CTLs generated from mice that were primed with ALVAC-F recombinant virus and boosted with the subunit vaccine (□), or primed and boosted with the ALVAC-F recombinant virus (Δ) or live mouse adapted virus (♦) lysed BCH4 cells (persistently infected with RSV) at all effector cell dilutions when compared to the lysis of BC (control) cells. CTL activity was not observed in animals that were primed and boosted with either the alum-adjuvanted RSV subunit vaccina or FI-RSV, Thus, priming animals with the ALVAC-F vector and boosting them with either the ALVAC-F vector or alum-adjuvanted RSV subunit vaccine induced significant levels of CTL activity.

EXAMPLE 8

The Example describes the protection of mice primed with ALVAC-F recombinant virus and boosted with RSV proteins.

Immunized mice were challenged intranasally with mouse-adapted RSV, A2 subtype. Lungs were aseptically removed about four days later, weighed and homogenized. The number of pfu in the lung homogenate was determined as described by Prince et al. (ref. 32) using VERO cells. The results are shown in Table 2 below.

In contrast to the placebo control animals (groups 6, 7, 8), the lower respiratory tract of mice that were primed with the ALVAC-F recombinant virus and boosted with the alum-adjuvanted RSV subunit preparation was completely protected against live virus challenge. Complete protection was also observed in animals that were immunized with two 1 µg doses of the alum-adjuvanted subunit vaccine or given live mouse-adapted RSV. Boosting ALVAC-F primed animals with the alum-adjuvanted subunit preparation resulted in a more durable protective response. It was observed that 3 out of 6 animals that were primed and boosted with the ALVAC-F recombinant virus had low, yet detectable levels of RSV in their lungs. In contrast, virus was not detected in the lungs of mice that were primed with the ALVAC-F recombinant virus and boosted with the subunit preparation.

SUMMARY OF DISCLOSURE

In summary of this disclosure, the present invention provides a novel immunization strategy to induce protection against paramyxoviridae virus disease, especially RSV which is safe and effective. Modifications are possible within the scope of this invention.

TABLE 1

| | | Immunization protocol | | |
|---|---|---|---|---|
| GROUP | PRIME | ROUTE OF INOCULATION | BOOST | ROUTE OF INOCULATION |
| 1 | ALVAC-F[1] | Intramuscular | Subunit Preparation[2] + alum | Intramuscular |
| 2 | ALVAC-F[1] | Intramuscular | ALVAC-F | Intramuscular |
| 3 | Subunit preparation + alum | Intramuscular | Subunit vaccine + alum | Intramuscular |
| 4 | Live RSV[3] | Intranasal | Live RSV | Intranasal |
| 5 | FI-RSV[4] + alum | Intramuscular | FI-RSV + alum | Intramuscular |
| 6 | Irrelevant ALVAC | Intramuscular | Irrelevant ALVAC | Intramuscular |

TABLE 1-continued

Immunization protocol

| GROUP | PRIME | ROUTE OF INOCULATION | BOOST | ROUTE OF INOCULATION |
|---|---|---|---|---|
| 7 | PBS + alum | Intramuscular | PBS + alum | Intramuscular |
| 8 | EMEM + 5% FBS + 5% glycerol | Intranasal | EMEM + 5% FBS + 5% glycerol | Intranasal |

Mice were inoculated with:
$^1 5 \times 10^7$ pfu of the ALVAC-F recombinant virus that was prepared according to the procedure outlined in Example 1
$^2 1$ μg of RSV subunit vaccine (Example 4) adsorbed to alum (1.5 mg/dose)
$^3 2.5 \times 10^5$ pfu of mouse-adapted A2 virus
$^4 100$ μl of 100 X formalin-inactivated (FI) RSV vaccine adsorbed to alum.

TABLE 2

Protective ablilty of the various RSV formulations in BALB/c mice

| Group # | Antigen Formulation Prime | Boost | Mean virus lung titre ($\log_{10}$/g ± s.d.) |
|---|---|---|---|
| 1 | ALVAC-F | Subunit preparaton + alum | ≦2.2 ± 0 |
| 2 | ALVAC-F | ALVAC-F | 2.4 ± 0.3 |
| 3 | Subunit preparation + alum | Subunit preparation + alum | ≦2.2 ± 0 |
| 4 | Live RSV | Live RSV | ≦2.2 ± 0 |
| 5 | FI-RSV | FI-RSV | 2.2 ± 0 |
| 6 | Irrelevant ALVAC | Irrelevant ALVAC | 5.2 ± 0.3 |
| 7 | PBS + alum | PBS + alum | 5.2 ± 0.2 |
| 8 | EMEM + 5% FBS + 5% glycerol | EMEM + 5% + 5% glycerol | 5.2 ± 0.4 |

REFERENCES

1. Glezen, W. P., Paredes, A. Allison, J. E., Taber, L. H. and Frank, A. L. (1981). J. Pediatr. 98, 708–715.
2. Chanock, R. M., Parrot, R. H., Connors, M., Collins, P. L. and Murphy, B. R. (1992) Pediatrics 90, 137–142.
3. Martin, A. J., Gardiner, P. S. and McQuillin, J. (1978). Lancet ii, 1035–1038.
4. Robbins, A., and Freeman, P. (1988) Sci. Am. 259, 126–133.
5. Glezen, W. P., Taber, L. H., Frank, A. L. and Kasel, J. A. (1986) Am. J. Dis. Child. 140, 143–146.
6. Katz, S. L. New vaccine development establishing priorities. Vol. 1. Washington: National Academic Press. (1985) pp. 397–409.
7. Wertz, G. W., Sullender, W. M. (1992) Biotech. 20, 151–176.
8. Fulginiti, V. A., Eller, J. J., Sieber, O. F., Joyner, i. W., Minamitani, M. and Meiklejohn, G. (1969) Am. J. Epidemiol. 89 (4), 435–448.
9. McIntosh, K. and Chanock, R. M. (1990) in Fields Virology (Fields, B. M., and Knipe D. M. eds.) pp. 1045–1075, Raven Press, Ltd., New York.
10. Cherrie, A. H., Anderson K, Wertz GW, and Openshaw PJM, 1992, J. Virology, 66: 2102–2110
11. Chin, J., Magoffin, R. L., Shearer, L. A., Schieble, J. H. and Lennette, E. H. (1969) Am. J. Epidemiol. 89 (4), 449–463.
12. Kapikian, A. Z., Mitchell, R. H., Chanock, R. M., Shvedoff, R. A. and Stewart, C. E. (1969) Am. J. Epidemiol. 89 (4), 405–421.
13. Connors, M., Collins, P. L., Firestone, C. Y., Sotnikov, A. V., Waitze, A., Davis, A. R., Hung, P. P., Chanock, R. M., Murphy, b. (1992) Vaccine, 10, 475–484.
14. Walsh, E. E., Hall, C. B., Briselli, M., Brandiss, M. W. and Schlesinger, J. J. (1987) J. Infect. Dis. 155 (6), 1198–1204.
15. Connors M, Kulkarni, CY, Firestone KL, Holmes KL, Morse III HC, Sotnikov AV, and Murphy BR, (1992). J. Virol. 66: 7444–7451.
16. Connors M, Giese NA, Kulkarni AB, Firestone CY, Morse III HC, and Murphy BR, (1994) J. Virol. 68: 5321–5325.
17. Waris, ME, Tsou C., Edrman DD, Zaki SR and Anderson., (1996), J. Virol. 70: 2852–2860.
18. Fenner, F., Henderson, D. A., Arita, I., Jezek, J., Ladnyi, I. D. (1988) Smallpox and its Eradication. Geneva. World Health Organization.
19. Tartaglia, J., Perkus, M. E., Taylor, J., Norton, E. K., audonnet, J. -C., Cox, W. I., Davis, S. W., VanderHoeven, J., Meignier, B., Riviere, M., Languet, B., Paoletti, E. (1992) NYVAC: a highly attenuated strain of vaccinia virus. Virology 188, 217–232.
20. Konishi, E., Pincus, S., Paoletti, E., Laegried, W. W., Shope, R. E., Mason, P. W. (1992) A highly attenuated host-range restricted vaccinia virus strain, NYVAC, encoding the prM, E, and NS1 genes of Japanese encephalitis virus prevents JEV viremia in swine. Virology 190, 454–458.
21. Taylor, J., Weinberg, R., Kawaoka, Y., Webster, R., Paoletti, E. (1988a) Protective immunity against avian influenza induced b a fowlpoxvirus recombinant. Vaccine 6, 504–508.
22. Taylor, J., Weinberg, R., Languet, B., Desmettre, Ph., Paoletti, E. (1988b) Recombinant fowlpoxvirus inducing protective immunity in non-avian species. Vaccine 6, 497–503.

23. Taylor, J., Trimarchi, C., Weinberg, R., Languet, B., Guillemin, F., Desmettre, Ph., Paoletti, E. (1991) Efficacy studies on a canarypox-rabies recombinant. Vaccine 9, 190–193.
24. Taylor, J., Weinberg, R., Tartaglia, J., Richardson. C., Alkatib, G., Briedis, D., Appel, M., Norton, E., Paoletti, E. (1992) Nonreplicating viral vectors as potential vaccines: recombinant canarypox virus expressing measles virus fusion (F) and hemagglutinin (HA) glycoproteins. Virology 187, 321–328.
25. Tartaglia, J., Taylor, J., Cox, W. I., Andonnet, J. -C., Perkus, M. E., Raedelli, A., de Giuli Morghen, C., Meignier, B., Riviere, M., Weinhold, K., Paoletti, E. (1993) Novel poxvirus strains as research tools and vaccine vectors. In AIDS Research Reviews (W. C. Koff, F. Wong-Staal, and R. C. kennedy, eds.), vol. 3 Marcel Dekkar, New York, 361–378.
26. Cadoz, M., Strady, A., Meignier, B., Taylor, J., Taryaglia, J., Paoletti, E., Plotkin, S. (1992) Immunization with canarypox virus expressing rabies glycoproteins, Lancet 339, 1429–1432.
27. Pialoux, G., Excler, J. -L., Riviere, Y., Gonzalez-Canali, G., Feuillia, V., Coulaud, P., Gluckman, J. -C., Matthews, T. J., Meignier, B., Kieny, M. -P., Gonnet, P., Diaz, I., Meric, C., Paoletti, E., Tartaglia, J., Salomon, H., Plotkin, S. (1995) A primeboost approach to HIV preventive vaccine using a recombinant canarypox virus expressing glycoprotein gp16O (MN) followed by a recombinant glycoprotein 160 (MN/Lai). AIDS Res. Hum. Retrovir. 11, 373–381.
28. Mullis, K., Ferre, F., and Gibbs, R. (1994) The Polymerase Chain Reaction, Boston: Birkhauser press.
29. Perkus, M., Limbach, K. and Paoletti, E. (1989) Cloning and expression of foreign genes in vaccinia virus, using a host range selection system. J. Virol. 63: 3829–3836.
30. Yuen, L. and Moss, B. (1987) PNAS 84: 6417–6421.
31. Goebel, S., Johnson, G., Perkus, M., Davis, S., Winslow, J., and Paoletti, E. (1990), The complete DNA sequence of vaccinia virus, Virology 179: 247–266.
32. Prince, G. A. et al. 1978, Am J. Pathol. 93: 771–790.
33. Fulginiti, V. A., Eller, J. J., Sieber, O. F., Joyner, J. W., Minamitani, M. and Meiklejohn, G. (1969) Am. J. Epidemiol. 89 (4), 435–448.
34. Chin, J., Magoffin, R. L., Shearer, L. A., Schieble, J. H. and Lennette, E. H. (1969) Am J. Epidemiol. 89 (4), 449–463.
35. Jensen, K. E., Peeler, B. E. and Dulworth, W. G. (1962) J. Immunol. 89, 216–226.
36. Murphy, B. R., Prince, G. A., Collins, P. L., Van Wyke Coelingh, K., Olmsted, R. A., Spriggs, M. K., Parrott, R. H., Kim, H. -Y., Brandt, C. D. and Chanock, R. M. (1988) Vir. Res. 11, 1–15.
37. Hall, S. L., Sarris, C. M., Tierney, E. L., London, W. T., and Murphy, B. R. (1993) J. Infect. Dis. 167, 958–962.
Belshe, R. B., Karron, R. A., Newman, F. K., Anderson, E. L., Nugent, S. L., Steinhoff, M., Clements, M. L., Wilson, M. H., Hall, S. L., Tierney, E. L. and Murphy B. R. (1992) J. Clin. Microbiol. 30 (8), 2064–2070.
39. Hall, S. L., Stokes, A., Tierney, E. L., London, W. T., Balshe, R. B., Newman, F. C. and Murphy, B. R. (1992) Vir. Res. 22, 173–184.
40. Van Wyke Coelingh, K. L., Winter, C. C., Tierney, E. L., London, W. T. and Murphy, B. R. (1988) J. Infect. Dis. 157 (4), 655–662.
41. Ray, R., Novak, M., Duncan, J. D., Matsuoka, Y. and Compans, R. W. (1993) J. Infect. Dis. 167, 752–755.
42. Ray, R., Brown, V. E. and Compans, R. W. (1985) J. Infect. Dis. 152 (6), 1219–1230.
43. Ray, R. and Compans, R. W. (1987) J. Gen. Virol. 68, 409–418.
44. Ray, R., Glaze, B. J., Moldoveanu, Z. and Compans, R. W. (1988) J. Infect. Dis. 157 (4), 648–654.
45. Ray, R., Matsuoka, Y., Burnett, T. L., Glaze, B. J. and Compans, R. W. (1990) J. Infect. Dis. 162, 746–749.
46. Ray, R., Glaze, B. J. and Compans, R. W. (1988) J. Virol. 62 (3), 783–787.
47. Ewasyshyn, M., Caplan, B., Bonneau A. -M., Scollard, N., Graham, S., Usman, S. and Klein, M. (1992) Vaccine 10 (6), 412–420.
48. Ambrose, M. W., Wyde, P. R., Ewasyshyn, M., Bonneau, A. -M., Caplan, B., Meyer, H. L. and Klein, M. (1991) Vaccine 9, 505–511.
49. Kasel, J. A., Frank, A. L., Keitel, W. H., Taber, L. H., Glezen W. P. J. Virol. 1984; 52:828–32.
50. Lehman, D. J., Roof, L. L., Brideau, R. J., Aeed, P. A., Thomsen, D. R., Elhammer, A. P., Wathen, M. W. and Homa, F. L. (1993) J. Gen. Virol. 74, 459–469.
51. Brideau, R. J., Oien, N. L., Lehman, D. J., Homa, F. L. and Wathen, M. W. (1993) J. Gen. Virol. 74, 471–477.
52. Ebata, S. N., Prevec, L., Graham, F. L. and Dimock, K. (1992) Vir. Res. 24, 21–35.
53. Hall, S. L., Murphy, B. R. and Van Wyke Coelingh, K. L. (1991) Vaccine 9, 659–667.

What we claim is:

1. A method of inducing an immune response in a host against disease caused by respiratory syncytial virus (RSV), which comprises:

initially administering to the host an immunoeffective amount of a recombinant virus vector expressing at least one RSV protein or immunogenic fragment thereof; and subsequently administering to the host an immunoeffective amount of at least one purified RSV protein or immunogenic fragment thereof to achieve a RSV specific immune response in the host.

2. The method of claim 1 wherein said immune response in the host includes the production of virus specific neutralizing antibodies and/or virus specific cytotoxic T-cell responses.

3. The method of claim 2 wherein said recombinant virus is a recombinant pox virus.

4. The method of claim 2 wherein said recombinant virus expresses at least one RSV protein or immunogenic fragment thereof selected from the group consisting of the fusion (F), attachment (G) and matrix (M) proteins.

5. The method of claim 2 wherein said at least one purified RSV protein or immunogenic fragment thereof is selected from the group consisting of the fusion (F), attachment (G) and matrix (M) proteins.

6. The method of claim 5 wherein said recombinant virus is a recombinant pox virus.

7. The method of claim 5 wherein said recombinant virus expresses at least one RSV protein or immunogenic fragment thereof selected from the group consisting of the fusion (F), attachment (G) and matrix (M) proteins.

8. The method of claim 1 wherein the at least one purified RSV protein or immunogenic fragment thereof is administered with an adjuvant.

9. The method of claim 8 wherein the adjuvant is alum.

* * * * *